(12) United States Patent
Ruecker et al.

(10) Patent No.: US 7,781,193 B2
(45) Date of Patent: Aug. 24, 2010

(54) SOLVENTLESS EXTRACTION PROCESS

(75) Inventors: Craig M. Ruecker, San Diego, CA (US); Swithwin Patrick Adu-peasah, San Diego, CA (US); Brian S. Engelhardt, San Diego, CA (US); George T. Veeder, III, Ramona, CA (US)

(73) Assignee: Martek Biosciences Corporation, Columbia, MD (US)

(*) Notice: Subject to any disclaimer, the term of this patent is extended or adjusted under 35 U.S.C. 154(b) by 0 days.

(21) Appl. No.: 11/782,416

(22) Filed: Jul. 24, 2007

(65) Prior Publication Data
US 2008/0044875 A1 Feb. 21, 2008

Related U.S. Application Data

(63) Continuation of application No. 10/784,148, filed on Feb. 20, 2004, now Pat. No. 7,351,558, which is a continuation of application No. 09/766,500, filed on Jan. 19, 2001, now Pat. No. 6,750,048.

(60) Provisional application No. 60/177,125, filed on Jan. 19, 2000.

(51) Int. Cl.
C12P 7/64 (2006.01)
C12P 1/00 (2006.01)
C12P 1/04 (2006.01)

(52) U.S. Cl. .................. 435/134; 435/170; 435/171; 435/173.9; 424/195.15; 424/195.16; 424/195.17; 424/780

(58) Field of Classification Search .................. 435/134, 435/17, 171, 173.9; 424/195.15, 195.16, 424/195.17, 780
See application file for complete search history.

(56) References Cited

U.S. PATENT DOCUMENTS

| | | | |
|---|---|---|---|
| 2,753,362 | A | 7/1956 | Owades et al. |
| 3,089,821 | A | 5/1963 | Folkers et al. |
| 4,504,473 | A | 3/1985 | Cantrell |
| 4,720,456 | A | 1/1988 | Wagner et al. |
| 4,792,418 | A | 12/1988 | Rubin et al. |
| 5,130,242 | A | 7/1992 | Barclay |
| 5,179,012 | A | 1/1993 | Gudin et al. |
| 5,340,594 | A | 8/1994 | Barclay |
| 5,397,591 | A | 3/1995 | Kyle et al. |
| 5,539,133 | A | 7/1996 | Kohn et al. |
| 5,928,696 | A | 7/1999 | Best et al. |
| 6,166,231 | A | 12/2000 | Hoeksema |
| 6,255,505 | B1 | 7/2001 | Bijl et al. |
| 6,750,048 | B2 | 6/2004 | Ruecker et al. |
| 7,351,558 | B2 | 4/2008 | Ruecker et al. |
| 2008/0038800 | A1 | 2/2008 | Ruecker et al. |
| 2008/0044876 | A1 | 2/2008 | Ruecker et al. |

FOREIGN PATENT DOCUMENTS

| | | |
|---|---|---|
| DE | 2056896 | 11/1970 |
| EP | 0969086 | 1/2000 |
| JP | 04-211366 | 8/1992 |
| JP | 8509355 | 10/1996 |
| JP | 10072590 | 3/1998 |
| JP | 11-116983 | 4/1999 |
| JP | 11-285376 | 10/1999 |
| WO | WO 88/08025 | 10/1988 |
| WO | WO 96/05278 | 2/1996 |
| WO | WO 98/03671 | 1/1998 |
| WO | WO 01/53512 | 7/2001 |
| WO | WO 97/04121 | 6/2007 |

OTHER PUBLICATIONS

Ayres et al., Letters Applied Microbiol., 27(6):372-374 (1998) Abstract.
Harrison et al., Bioseparation, 2(2):95-105 (1991).
International Preliminary Examination Report dated May 6, 2002 for International Patent Application No. PCT/US01/01806 (2997-19-PCT).
International Preliminary Examination Report dated Sep. 27, 2002 for International Patent Application No. PCT/US01/01806 (2997-19-PCT).
International Search Report dated May 22, 2001 for International Patent Application No. PCT/US01/01806 (2997-19-PCT).
Medina et al., Biotech.Adv., 16(3):517-580 (1998).
Privett et al., Progr. Chem. Fats Lipids, 9(P43), 407-52 (1968).
Redman et al., "Phospholipid metabolism in intact and modified erythrocyte membrane" The Journal of Cell Biology, vol. 49(1): 35-49, published Apr. 1971.

(Continued)

Primary Examiner—Ruth A Davis
(74) Attorney, Agent, or Firm—Sterne, Kessler, Goldstein & Fox P.L.L.C.

(57) ABSTRACT

The present invention provides a method for extracting lipids from microorganisms without using organic solvent as an extraction solvent. In particular, the present invention provides a method for extracting lipids from microorganisms by lysing cells and removing water soluble compound and/or materials by washing the lysed cell mixtures with aqueous washing solutions until a substantially non-emulsified lipid is obtained.

24 Claims, 1 Drawing Sheet

OTHER PUBLICATIONS

Sawayama et al., "Possibility of renewable energy production and CO2 mitigation by thermochemical liquefaction of microalgae", Biomass and Bioenergy, vol. 17(1): 33-39, published Jul. 1999.

Supplementary Partial European Search Report for European Patent Application No. 01942672.5-2406, mailed Jul. 30, 2004 (2997-19-PEP).

Written Opinion dated Sep. 25, 2001 in International Patent Application No. PCT/US01/01806 (2997-19-PCT).

SOLVENTLESS EXTRACTION PROCESS

CROSS-REFERENCE TO RELATED APPLICATIONS

This application is a continuation of prior pending U.S. application Ser. No. 10/784,148, filed Feb. 20, 2004, which is a continuation of U.S. application Ser. No. 09/766,500, filed Jan. 19, 2001, which claims the benefit of priority under 35 U.S.C. §119(e) from Provisional Patent Application Ser. No. 60/177,125, filed on Jan. 19, 2000. Each of the foregoing applications is incorporated herein by reference in its entirety.

FIELD OF THE INVENTION

The present invention is directed to a process for extracting lipids from microorganisms without the use of any significant amount of an organic solvent.

BACKGROUND OF THE INVENTION

A typical microorganism lipid manufacturing process, such as production of omega-3 highly unsaturated fatty acid, in particular docosahexaenoic acid (DHA), involves growing microorganisms which are capable of producing the desired lipid in a fermentor, pond or bioreactor, isolating the microbial biomass, drying it, and extracting intracellular lipids with an organic solvent, e.g., hexane. Generally, intracellular lipids of microorganisms are extracted after rupturing (i.e., lysing) the cells of the microorganisms. The extracted lipids are can be further refined to produce a high purity and/or quality lipids. The microorganisms are generally isolated by first diluting the fermentation broth with water, and centrifuging the mixture to isolate microorganisms. When lipids are not extracted immediately or soon after isolating the microorganisms, the isolated microorganisms are typically dried, for example, on a drum dryer, and packaged, for example, in vacuum-sealed bags, to prevent degradation of lipids.

Unfortunately, the drying process exposes the microorganisms to heat, which can damage, i.e., degrade the quality of, lipids if done incorrectly. The vacuum-sealed bags may develop leaks, which can further degrade the quality of the lipids due to exposure of the microorganisms to air. In addition, if the dried microorganisms are not treated with an antioxidant, lipids can be further degraded due to exposure to air, for example, DHA may degrade due to oxidation by air. Furthermore, in some cases operators who are exposed to the dried microorganisms can develop an allergic reaction creating a safety and/or health hazard to operators.

Moreover, in an industrial scale production, the amount of organic solvent used in lipid extraction typically requires a large amount of volatile and flammable organic solvent, thereby creating hazardous operating conditions. The use of organic solvent in the extraction process may necessitate using an explosion-proof oil recovery system, thereby adding to the cost of lipid recovery. Moreover, use of an organic solvent in extracting lipids from microorganisms generate an organic solvent waste stream requiring a proper method, which further increases the overall production cost of lipid extraction.

Therefore, there is a need for a process for extracting lipids from microorganisms which does not require the use of an organic solvent. There is also a need for a lipid extraction process from microorganisms which does not require the expensive step of drying the microorganisms.

SUMMARY OF THE INVENTION

The present invention provides a process for obtaining lipid from microorganisms comprising:
(a) lysing cells of the microorganisms to produce a lysed cell mixture;
(b) treating the lysed cell mixture to produce a phase separated mixture comprising a heavy layer and a light layer;
(c) separating the heavy layer from the light layer; and
(d) obtaining the lipid from the light layer.

The lysed cell mixture may contain an emulsion, in which case the emulsion can be separated by centrifuging the lysed cell mixture. The separated lysed cell mixture comprises a heavy layer which contains aqueous solution and a light layer which contains lipids, which may be emulsified. The aqueous solution comprises solid cell materials which results from lysing cells. The light layer can be further washed with an aqueous washing solution until the lipid becomes substantially non-emulsified.

When the lipid extraction process of the present invention includes using microorganisms from a fermentation process, the extraction process can also include solubilizing at least part of proteinaceous compounds in a fermentation broth, by adding a base selected from the group consisting of hydroxides, carbonates, bicarbonates and mixtures thereof.

The process of the present invention can also include heating the microorganisms to temperature of at least about 50° C.

Preferably, the microorganisms are capable of growth at salinity level of less than about 12 g/L of sodium chloride, more preferably less than about 5 g/L of sodium chloride and most preferably less than about 3 g/L of sodium chloride.

Preferably, the microorganisms comprise at least about 30% by weight of lipid, more preferably at least about 35% by weight, and most preferably at least about 40%. Alternatively at least about 30% of the lipid is docosahexaenoic acid, preferably at least about 35%, and more preferably at least about 40%.

In one particular aspect of the present invention the microorganisms are capable of producing at least about 0.1 grams per liter per hour of docosahexaenoic acid, more preferably at least about 0.2 g/L/h, still more preferably at least about 0.3 g/L/h, and most preferably at least about 0.4 g/L/h.

In another aspect of the present invention, the microorganism is selected from the group consisting of algae, fungi, bacteria and protist. Preferably, the microorganisms are of the order Thraustochytriales. More preferably the microorganisms are selected from the genus *Thraustochytrium, Schizochytrium* and mixtures thereof. And most preferably, the microorganisms are selected from the group consisting of microorganisms having the identifying characteristics of ATCC number 20888, ATCC number 20889, ATCC number 20890, ATCC number 20891 and ATCC number 20892, mutant strains derived from any of the foregoing, and mixtures thereof.

DETAILED DESCRIPTION OF THE INVENTION

Figure 1:
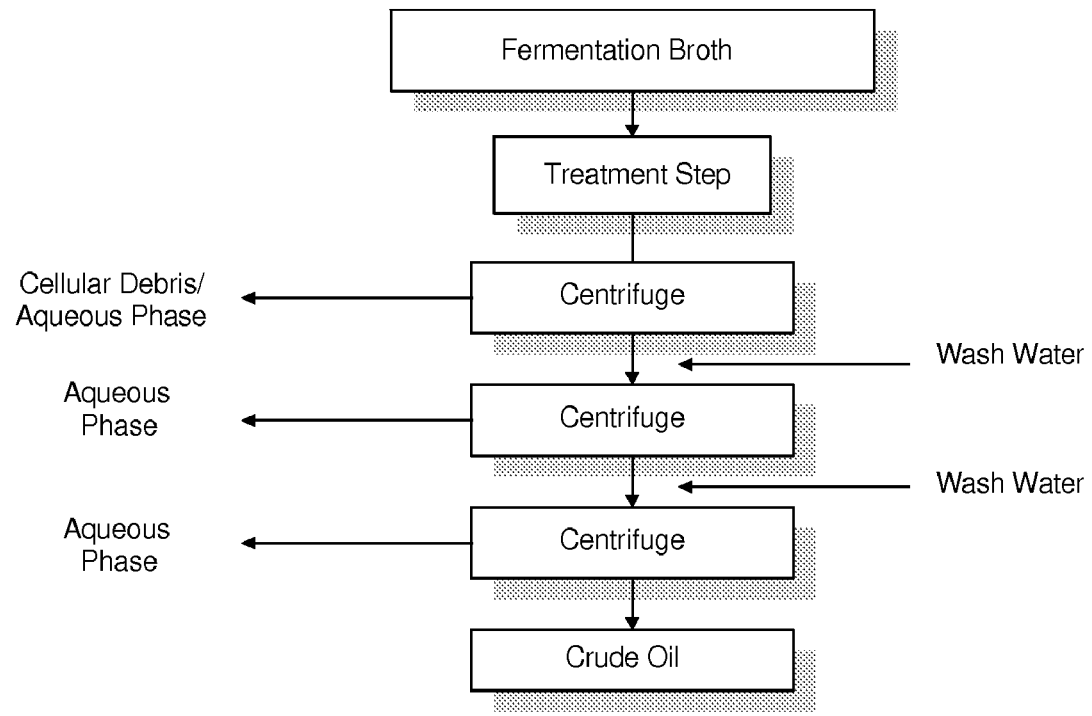
FIG. 1 is a flow diagram of one embodiment of a solventless extraction process of the present invention.

The present invention is directed to a process for extracting, recovering, isolating or obtaining lipids from microorganisms. The process of the present invention is applicable to extracting a variety of lipids from a variety of microorganisms, for example, extracting lipids containing omega-3 highly unsaturated fatty acids, such as docosahexaenoic acid (DHA), eicosapentaenoic acid (EPA), and/or docosapentaenoic acid (DPA), in particular lipids containing a relatively large amount of DHA, from microorganisms producing the same and extracting lipids containing arachidonic acid from microorganisms producing the same. Exemplary microorganisms which produce a relatively large amount of omega-3 highly unsaturated fatty acids are disclosed in commonly assigned U.S. Pat. Nos. 5,340,594 and 5,340,742, both issued to Barclay, and exemplary microorganisms which produce a relatively large amount of arachidonic acid are disclosed in commonly assigned U.S. Pat. No. 5,583,019, issued to Barclay. All of the above disclosed patents are incorporated herein by reference in their entirety.

For the sake of brevity, however, this detailed description of the invention is presented for purposes of convenience and illustration for the case of extracting lipids comprising omega-3 highly unsaturated fatty acid from microorganisms producing the same, in particular extracting lipids from microorganisms which produce a relatively high amount of DHA. It is to be understood, however, that the invention as a whole is not intended to be so limited, and that one skilled in the art will recognize that the concept of the present invention will be applicable to other microorganisms producing a variety of lipid compositions in accordance with the techniques discussed herein. These microorganisms include microorganisms, such as fungi, protist, algae and bacteria, which produce a variety of lipids, such as phospholipids; free fatty acids; esters of fatty acids, including triglycerides of fatty acids; sterols; pigments (e.g., carotenoids and oxycarotenoids) and other lipids, and lipid associated compounds such as phytosterols, ergothionine, lipoic acid and antioxidants including beta-carotene and tocopherol. Exemplary lipids include, but are not limited to, arachidonic acid, stearidonic acid, cholesterol, desmesterol, astaxanthin, canthaxanthin, and n-6 and n-3 highly unsaturated fatty acids such as eicosapentaenoic acid, docosapentaenoic acid and docosahexaenoic acid. For the sake of brevity, unless otherwise stated, the term "lipid" refers to lipid and/or lipid associated compounds. Other lipids and microorganisms which may be suitable for use in the instant invention will be readily apparent to those skilled in the art.

Typical microbial lipid (in particular an oil containing an omega-3 highly unsaturated fatty acid such as DHA) manufacturing processes involve growing microorganisms which produce DHA in a fermentor, isolating the microorganisms, and extracting the intracellular lipids with organic solvent, e.g., hexane. The extracted lipid is generally further refined to produce a high purity and/or quality lipid. The isolation of microorganisms involves diluting the fermentation broth with water and centrifuging the mixture to isolate microorganisms. When lipids are not extracted immediately or soon after isolating the microorganisms, the isolated microorganisms are typically dried, for example, on a drum dryer, and sealed in a package, e.g., in vacuum-sealed bags, to prevent degradation of lipids. Unfortunately, the drying process exposes the microorganisms to heat, which can damage, i.e., degrade the quality of, the lipid if done incorrectly. The package may develop leaks, which can further degrade the quality of the lipids. Furthermore, if the dried microorganisms are not treated with an antioxidant, the exposure of microorganisms to air can further degrade lipids.

Recovering the crude oil directly from the fermentation broth avoids these problems. Avoiding the organic solvent extraction step reduces manufacturing costs and also eliminates operator exposure to the dried microorganisms, which can cause an allergic response in some individuals.

The present invention provides a method for obtaining lipids from microorganisms using a substantially organic solvent free extraction process, i.e., a "solventless" extraction process. The term "solventless extraction process" refers to an extraction process which when an aqueous solvent is used, the aqueous solvent comprises less than about 5% of an organic solvent, preferably less than about 4%, more preferably less than about 2%, and most preferably less than 1%. The process of the present invention can include obtaining or isolating microorganisms, preferably from a fermentation process. In contrast to the current methods, the process of the present invention does not require a drying step prior to the extraction process. Thus, processes of the present invention are applicable to extracting lipids from a microbial biomass containing at least about 10% by weight entrained water, preferably at least about 20%, more preferably at least about 30%, and most preferably at least about 50%. When the microorganisms are obtained from a fermentation process, the process of the present invention can include adding a base to the fermentation broth to dissolve any proteinaceous compound that may be present in the broth. A "base" refers to any compound whose pKa is greater than that of water. The base should be strong enough to hydrolyze at least a portion of proteinaceous compounds that may be present in the broth. Bases which are useful for solubilizing proteins are well known to one of ordinary skill in the art of chemistry. Exemplary bases which are useful in the processes of the present invention include, but are not limited to, hydroxides, carbonates and bicarbonates of lithium, sodium, potassium, calcium, and magnesium carbonate.

The process of the present invention can also include rupturing or lysing the cells of microorganisms to release the lipids which are present within the cells. Cells can be lysed using any of the known methods including chemical; thermal; mechanical, including, but not limited to, french press, mills, ultrasonication, and homogenization; and combinations thereof. In a thermal lysing of cells, the fermentation broth containing microorganisms are heated until cells, i.e., cell walls, of microorganisms degrade or breakdown. Typically, the fermentation broth is heated to a temperature of at least about 50° C., preferably at least about 75° C., more preferably to at least about 100° C., and most preferably to at least about 130° C. Thermally lysing the cell walls of microorganisms is particularly useful for microorganisms whose cell walls are composed of proteins.

Heating the broth also denatures proteins and helps solubilize organic materials, including proteins. Heating of the fermentation broth step can be achieved by any of the known methods, including the use of an in-line heat exchanger, and preferably by sparging steam into the fermentor and maintaining the broth at a desired temperature for less than about 90 minutes, preferably less than about 60 minutes, and more preferably less than about 30 minutes.

The solventless extraction process of the present invention can also include at least partially separating the broth from lipids. Typically, this is achieved by centrifuging, e.g., by passing the broth through a stacked-disc centrifuge, and collecting lipids as an emulsion phase. Centrifuging the mixture results in a two phase mixture comprising a heavy layer and a light layer. Typically, the heavy layer is an aqueous phase, which contains the majority of cellular debris. The light layer which contains emulsified lipids is then diluted with water, again separated into two phase mixture and the light layer is again isolated. This dilution with water, separation and isolation processes (i.e., washing process) can be achieved continuously by feeding water and removing the heavy layer throughout the process or it can be conducted in discreet steps. The washing process is generally repeated until a non-emulsified lipid layer is obtained. It is believed that the oil-water interface of the emulsion is stabilized by residual cellular debris which is removed by the washing process. During the washing process, the successive amount of water added is reduced to increase the lipid content. While reducing the amount of feed water too quickly can result in loss of lipids to the aqueous phase, reducing the amount of feed water too slowly results in an inefficient washing process. One can readily determine an appropriate rate of feed water reduction by observing or analyzing the separated aqueous layer. Generally, the lipid layer, i.e., the light layer, is colored; therefore, in many cases one can determine an appropriate rate of feed water reduction by simply analyzing or observing the color of the aqueous layer which is separated from the lipid layer.

The isolated lipid can be further refined using a process similar to that used to refine standard vegetable oils. Briefly, the lipid refining process generally involves hydrating phospholipids by adding phosphoric acid to the lipid followed by adding sodium hydroxide to neutralize free fatty acids. These compounds are removed via centrifugation. This is then followed by a water wash step to further remove any remaining amounts of hydrated phospholipids ("gums") and neutralized fatty acids ("soapstock") in the lipid. The resulting lipid is bleached using Trysil™ and a standard bleaching clay. Citric acid is also added to remove divalent metal ions by chelation. The Trysil™ and bleaching clay are then removed via filtration to produce refined lipid. The bleached lipid can be cold filtered to remove high melting point compounds that may be present in the lipid; however, this step is generally seldom required.

The resulting lipid can be further refined by removing any low molecular weight components that may be present. Typically, these components are removed by sparging with steam at high temperatures, under high vacuum. This process also destroys any peroxide bonds which may be present and reduces or removes off odors and helps improve the stability of the oil. An antioxidant may then be added to the resulting deodorized lipid to improve product stability.

Prior to the refining process, the isolated lipid can be winterized to remove high melting compounds, such as saturated fatty acids. The winterization process generally involves dissolving the isolated lipid in an organic solvent, e.g., hexane, cooling the resulting organic solution, and filtering the solution to remove the high melting point components of the lipid or stearine phase. The winterization process generally produces a clear lipid, especially when the isolated lipid is cloudy or opaque.

While, the process of the present invention can include isolating microorganisms from a fermentation process, one of the advantages of the present invention is that it allows fermentation of microorganisms and isolation of lipids to be carried out in a single vessel. For example, after the fermentation, one can add base to the fermentation vessel and heat the mixture to lyse cells. After separating the phase into a heavy layer and a light layer, the light layer can be transferred to another vessel for further processing or the heavy layer can be removed from the fermentation vessel, for example, by draining through the bottom of the fermentation vessel, and the remaining light layer can be further processed within the same fermentation vessel.

Additional objects, advantages, and novel features of this invention will become apparent to those skilled in the art upon examination of the following examples thereof, which are not intended to be limiting.

EXAMPLES

Process reproducibility was characterized by producing three samples of fully refined oil using crude oil from the new solventless extraction process. A hexane-extracted sample was also fully refined to serve as a control. The fermentation, extraction and oil isolation steps were performed at a large scale, while the oil refining studies were performed at a small scale.

The fully refined oil samples were analyzed to demonstrate process reproducibility.

Fermentation:

A single F-Tank batch (~1,200 gallons) was used to generate the starting broth for the three solventless extraction processes. The batch (#F99202) was allowed to run for 94 hours, while controlling the glucose levels at 13 g/L, after which time the corn syrup feed was terminated. Residual glucose levels dropped to <5 g/L four hours later. This resulted in a final age of 98 hours. The final broth volume was 958 gallons. The final yield was 146 g/L. Both in-process contamination checks and a thorough analysis of a final broth sample failed to show any signs of contamination.

Hexane-Extracted Control Sample:

A small aliquot of broth from batch #F99202 was drum-dried and extracted with hexane to serve as a control sample. The biomass intermediate (DHAINT Lot #9F0067A) was recovered using a 66 ft$^2$ double-drum dryer. Analysis of this lipid is shown in Table 1.

TABLE 1

| Analysis of DHAINT Lot #9F0067A. | |
|---|---|
| Parameter | Value |
| DHA Content (FAME basis) | 35.7% |
| Oil Content | 62.7% |
| Peroxide Value (meq/kg) | 2.6 |
| Total Plate Count (cfu/g) | <50 |
| DHA Content* | 20.3% |
| FAME Content | 56.9% |

*cellular dry weight basis

Solventless Extraction Process:

Crude oil was obtained by treating three 400-gallon aliquots (approx.) of broth in batch #F99202. Each 400-gallon aliquot from the F-Tank batch was processed separately, starting with the caustic/heat treatment steps. Each aliquot was treated with 20 grams of 45% KOH per liter and heated to 130° C. for about 30 minutes by passing stream through the fermentation broth. The crude oil was recovered from the treated broth using a commercial-scale Westfalia HFA-100 stacked-disc centrifuge. Summary results for various process parameters are reported in Table 2, and the final crude oil analysis results are shown in Table 3.

TABLE 2

Process Data from the Solventless Extraction Process.

|  | SFE-1 | SFE-2 | SFE-3 |
|---|---|---|---|
| Broth Treatment | | | |
| Volume of Broth Processed | 288 gal | 288 gal | 258 gal |
| Final Treated pH | 7.5 | 8.0 | 8.7 |
| Final Volume After Heat Treatment | 388 gal | 398 gal | 308 gal |
| Volume Increase From Condensate | 34.7% | 38.2% | 19.4% |
| 1st Pass Emulsion | | | |
| Total Volume (gal) | 180 | 133 | 149 |
| Est. Oil Concentration (w/w) | 12.0% | 24.5% | 16.1% |
| Apparent Density (g/mL) | 0.986 | 0.991 | 0.999 |
| Oil Isolation | | | |
| Total Crude Oil Recovered (lb) | 182 | 165 | 174 |
| DHAOIL Lot Number Assigned | 9F0001A | 9F0002A | 9F0003A |

TABLE 3

Analysis of Lots of DHA from the Solventless Extraction Process.

| Parameter | 9F0001A | 9F0002A | 9F0003A |
|---|---|---|---|
| DHA Content (% FAME) | 39.0% | 38.6% | 39.2% |
| Peroxide Value (meq/kg) | 4.6 | 1.8 | 2.0 |
| Acid Value (mg KOH/g) | N/D | N/D | N/D |
| Moisture Content | N/D | N/D | N/D |

Refining:

A sample from each aliquot of crude oil was winterized, refined, bleached and deodorized at a small scale, as was a sample of the crude oil from the hexane-extracted control. Miscellaneous process data from these small scale experiments is shown in Table 4, including recovery efficiencies for the various processing steps. While it is difficult to read too much into recovery efficiencies for bench-scale processes, as losses tend to be disproportionately large, the values listed in Table 4 show that values for the solventless-extracted samples tend to bracket the values measured for the hexane-extracted control, with the one exception being the winterization step. While the recovery efficiency during the winterization step for the hexane control was lower than those observed for the other three samples, this difference is insignificant from a statistical perspective. The high losses during the winterization step caused the overall recovery efficiency for the hexane-control sample to be lower as well. The lower yield would not be expected to have a significant impact on the overall quality of the oil. All in all, differences in the processing of the various oil samples were minimal.

TABLE 4

Miscellaneous Process Data from the Oil Refining Steps.

|  | HEX-1 | SFE-1 | SFE-2 | SFE-3 |
|---|---|---|---|---|
| Processing Conditions | | | | |
| Miscella Concentration | 45.0% | 52.9% | 52.8% | 45.0% |
| Steam Sparge Rate | 3.4% | 3.4% | 2.5% | 2.2% |
| Recovery Efficiencies | | | | |
| Winterization | 80.6% | 92.3% | 87.7% | 85.5% |
| Refining | 89.4% | 84.8% | 91.8% | 95.0% |
| Water Wash | 90.6% | 94.5% | 95.8% | 81.2% |
| Bleaching | 86.1% | 89.2% | 87.3% | 84.1% |

TABLE 4-continued

Miscellaneous Process Data from the Oil Refining Steps.

|  | HEX-1 | SFE-1 | SFE-2 | SFE-3 |
|---|---|---|---|---|
| Deodorization | 97.4% | 96.1% | 97.2% | 97.5% |
| Packaging | 88.2% | 89.7% | 89.3% | 95.8% |
| Overall | 48.2% | 56.9% | 58.5% | 51.8% |
| Final Product | | | | |
| Lot Number | 9F0009A | 9F0010A | 9F0011A | 9F0012A |

Fully refined oil samples from the three solventless extraction runs, and the hexane-extracted control, were analyzed and the results are shown in Table 5. Also shown are the corresponding release specifications for each parameter.

A sample of the starting crude oil from the solventless extraction run was also analyzed for iron content. The iron content of this sample (DHAOIL Lot #9F0002P) was 0.08 ppm. The concentration of the other trace metals was all below their respective detection limits.

TABLE 5

QC Results for RBD Oil from the Solventless Extraction Process.

|  | Hexane | Solventless Extraction | | |
|---|---|---|---|---|
| Run ID # | HEX-1 | SFE-1 | SFE-2 | SFE-3 |
| DHALIP-NS Lot # | 9F0009A | 9F0010A | 9F0011A | 9F0012A |
| Peroxide Value (meq/kg) | 0.28 | 0.69 | 0.35 | 0.34 |
| Acid Value (mg KOH/g) | 0.17 | 0.11 | 0.57 | 0.24 |
| Moisture & Volatiles | 0.00% | 0.06%** | 0.00% | 0.00% |
| Trace Metals (ppm) | | | | |
| Lead | <0.20 | <0.20 | <0.20 | <0.20 |
| Arsenic | <0.20 | <0.20 | <0.20 | <0.20 |
| Iron | 0.22 | 0.21 | 0.56*** | 0.02 |
| Copper | <0.05 | <0.05 | <0.05 | <0.05 |
| Mercury | <0.20 | <0.20 | <0.20 | <0.20 |
| DHA (% FAME) | 36.9 | 37.3 | 37.0 | 37.7 |
| DHA (mg/g oil) | 342 | 345 | 343 | 351 |
| Hexane (ppm) | <3 | <3 | <3 | <3 |

*Value was reduced to 0.22 mg KOH/g after repeating the refining and bleaching steps
**Sample analyzed by the San Diego Fermentation Sciences Analytical Group.
***Value was reduced to <0.02 ppm after repeating the refining and bleaching steps Shown in Table 6 is a more direct comparison of the average analysis results for the three samples from the solventless extraction process versus those for the hexane control.

TABLE 6

Comparison of Average Values.

|  | Hexane | Solventless Extraction | | | |
|---|---|---|---|---|---|
| Parameter | Control | Mean | Std Dev | CV | % Diff |
| Peroxide Value (meq/kg) | 0.28 | 0.46 | 0.20 | 43.3% | 64.3% |
| Acid Value (mg KOH/g) | 0.17 | 0.19* | 0.06 | 33.3% | 11.2% |
| Moisture & Volatiles | 0.00% | 0.02% | 0.03% | 173% | ND |
| Trace Metals (ppm) | | | | | |
| Lead | <0.20 | <0.20 | N/A | N/A | 0.0% |
| Arsenic | <0.20 | <0.20 | N/A | N/A | 0.0% |

TABLE 6-continued

Comparison of Average Values.

| Parameter | Hexane Control | Solventless Extraction | | | |
|---|---|---|---|---|---|
| | | Mean | Std Dev | CV | % Diff |
| Iron | 0.22 | 0.26 | 0.27 | 104% | 18.2% |
| Copper | <0.05 | <0.05 | N/A | N/A | 0.0% |
| Mercury | <0.20 | <0.20 | N/A | N/A | 0.0% |
| DHA Content (% FAME) | 36.9% | 37.3% | 0.4% | 0.9% | 1.1% |
| DHA Content (mg/g) | 342 | 346 | 4 | 1.2% | 1.2% |
| Hexane (ppm) | <3 | <3 | N/A | N/A | 0.0% |

*Calculated using the acid value for the re-worked sample.

The results from this experiment clearly demonstrate that the solventless extraction process is both reproducible and lipids from solventless extraction are relatively indistinguishable from the lipids obtained from hexane extraction process in terms of process performance and product quality. The final product from the solventless extraction process is substantially equivalent to lipids from a current hexane-based extraction process, as determined by similarities between the fatty acid and sterol profiles of the product from these two processes.

The present invention, in various embodiments, includes components, methods, processes, systems and/or apparatus substantially as depicted and described herein, including various embodiments, subcombinations, and subsets thereof. Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, e.g., for improving performance, achieving ease and\or reducing cost of implementation.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A process for obtaining lipids from microorganisms comprising:
   (a) releasing intracellular lipids of cells of the microorganisms grown in a fermentation medium into the fermentation medium by lysing the cells, rupturing the cells, or permeabilizing the cells;
   (b) producing a phase separated mixture from the fermentation medium comprising a heavy layer and a light layer, wherein said heavy layer comprises an aqueous solution and said light layer comprises said lipids;
   (c) separating said heavy layer from said light layer; and
   (d) obtaining said lipids from said light layer.

2. The process of claim 1, wherein said step (b) comprises centrifuging said lysed cell mixture.

3. The process of claim 2, wherein said light layer comprises an emulsified lipid.

4. The process of claim 3 further comprising:
   (e) adding an aqueous extraction solution to said light layer of step (c); and
   (f) repeating said steps (b), (c) and (e) until said lipid becomes substantially non-emulsified prior to said step (d).

5. The process of claim 3, wherein said emulsified lipid comprises a suspension of said lipid in an aqueous solution.

6. The process of claim 1, wherein said aqueous solution comprises solid cell materials.

7. The process of claim 1 further comprising adding a base to a fermentation broth.

8. The process of claim 7, wherein said base is selected from the group consisting of hydroxides, carbonates, bicarbonates, and mixtures thereof.

9. The process of claim 1 further comprising solubilizing at least part of proteinaceous compounds in the fermentation medium.

10. The process of claim 1, wherein said step (a) comprises heating said microorganisms to a temperature of at least about 50° C.

11. The process of claim 1, wherein said microorganism is capable of growth at a salinity level of less than about 12 g/L of sodium chloride.

12. The process of claim 1, wherein said microorganism comprises at least about 30% by weight of lipid.

13. The process of claim 1, wherein said microorganism is selected from the group consisting of algae, fungi, bacteria and protist.

14. The process of claim 13, wherein said microorganisms comprise microorganisms of the order Thraustochytriales.

15. The process of claim 14, wherein said microorganisms are selected from the genus *Thraustochytrium*, *Schizochytrium* and mixtures thereof.

16. The process of claim 15, wherein said microorganisms are selected from the group consisting of microorganisms having the identifying characteristics of ATCC number 20888, ATCC number 20889, ATCC number 20890, ATCC number 20891, ATCC number 20892, and mutant strains derived from any of the foregoing.

17. The process of claim 1, wherein said microorganisms are capable of producing at least about 0.1 grams per liter per hour of docosahexaenoic acid.

18. The process of claim 1, wherein at least about 30% of said lipid is docosahexaenoic acid.

19. The process of claim 1, wherein the step of producing is conducted in less than about 5% of an organic solvent.

20. The process of claim 19, wherein the organic solvent is hexane.

21. The process of claim 1, wherein the step of producing is conducted in less than about 4% of an organic solvent.

22. The process of claim 1, wherein the step of producing is conducted in less than about 2% of an organic solvent.

23. The process of claim 1, wherein the step of producing is conducted in less than about 1% of an organic solvent.

24. The process of claim 1, wherein the step of producing is conducted in the absence of an organic solvent.

* * * * *

UNITED STATES PATENT AND TRADEMARK OFFICE
CERTIFICATE OF CORRECTION

PATENT NO. : 7,781,193 B2 Page 1 of 1
APPLICATION NO. : 11/782416
DATED : August 24, 2010
INVENTOR(S) : Ruecker et al.

It is certified that error appears in the above-identified patent and that said Letters Patent is hereby corrected as shown below:

On the Title Page, Item (75)
In the Inventors, delete "Swithwin Patrick Adu-peasah" and insert --Swithin Patrick Adu-peasah--.

Signed and Sealed this

Sixteenth Day of November, 2010

David J. Kappos
*Director of the United States Patent and Trademark Office*